(12) United States Patent
Perlroth et al.

(10) Patent No.: US 10,706,964 B2
(45) Date of Patent: Jul. 7, 2020

(54) CONSTRAINED OPTIMIZATION FOR PROVIDER GROUPS

(71) Applicant: Lyra Health, Inc., Burlingame, CA (US)

(72) Inventors: Daniella J. Perlroth, Palo Alto, CA (US); Aaron Archer Waterman, Mountain View, CA (US); Jessie M. Burger, Mountain View, CA (US); Armando Franco, San Francisco, CA (US)

(73) Assignee: LYRA HEALTH, INC., Burlingame, CA (US)

( * ) Notice: Subject to any disclaimer, the term of this patent is extended or adjusted under 35 U.S.C. 154(b) by 393 days.

(21) Appl. No.: 15/339,803

(22) Filed: Oct. 31, 2016

(65) Prior Publication Data
US 2018/0121619 A1 May 3, 2018

(51) Int. Cl.
*G16H 40/20* (2018.01)
*G16H 50/20* (2018.01)

(52) U.S. Cl.
CPC ............. *G16H 40/20* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 2006/0025971 A1* | 2/2006 | Detwiler | G06F 30/13 703/1 |
| 2006/0161456 A1* | 7/2006 | Baker | G06Q 50/22 705/2 |
| 2007/0250352 A1* | 10/2007 | Tawil | G06Q 10/10 705/4 |
| 2009/0125348 A1* | 5/2009 | Rastogi | G06Q 30/018 705/7.32 |
| 2010/0235178 A1* | 9/2010 | Firminger | G06Q 10/06375 705/2 |
| 2012/0078664 A1* | 3/2012 | Hasan | G06F 19/324 705/3 |
| 2012/0166218 A1* | 6/2012 | Reiner | G16H 10/20 705/2 |
| 2014/0100882 A1* | 4/2014 | Hamilton | G06Q 30/0201 705/3 |

(Continued)

*Primary Examiner* — Michael Tomaszewski
*Assistant Examiner* — Jay M. Patel
(74) *Attorney, Agent, or Firm* — Fenwick & West LLP

(57) ABSTRACT

An optimization system optimizes groups of providers for a given population of users. The optimization system includes various engines such as a source interface engine, selection engine, and group score engine. The source interface engine receives information to be used in constrained optimization from server computers and stores the information in databases. The selection engine selects groups of providers from a set of all available providers. The group score engine generates a score for each group of providers. The selection engine continues to iteratively select groups of providers to minimize the generated score. The selection engine can use hard constraints, for example, requiring that a certain type of provider be included in all selected groups, or soft constraints, for example, requiring that a certain number of providers be included based on a size of the given population.

17 Claims, 9 Drawing Sheets

(56) References Cited

U.S. PATENT DOCUMENTS

| | | | | |
|---|---|---|---|---|
| 2014/0122100 | A1* | 5/2014 | Fillmore | G06Q 50/22 705/2 |
| 2014/0236630 | A1* | 8/2014 | Murata | G06Q 10/06398 705/3 |
| 2014/0365234 | A1* | 12/2014 | Saunders | G06F 19/3418 705/2 |
| 2015/0073833 | A1* | 3/2015 | Norris | G06F 16/24575 705/3 |
| 2015/0100336 | A1* | 4/2015 | Ford | G06Q 10/06393 705/2 |
| 2015/0278222 | A1* | 10/2015 | Claussenelias | G06F 16/24578 707/723 |
| 2016/0110657 | A1* | 4/2016 | Gibiansky | G06N 20/00 706/12 |

\* cited by examiner

400

```
┌─────────────────────────────────────────────────────────┐
│ Receive patient information describing a set of patients.│
│ 410                                                      │
└─────────────────────────────────────────────────────────┘
                          ▼
┌─────────────────────────────────────────────────────────┐
│ Receive health guidelines.                               │
│ 420                                                      │
└─────────────────────────────────────────────────────────┘
                          ▼
┌─────────────────────────────────────────────────────────┐
│ Identify a patient population having health needs.       │
│ 430                                                      │
└─────────────────────────────────────────────────────────┘
                          ▼
┌─────────────────────────────────────────────────────────┐
│ Receive health provider information describing health providers. │
│ 440                                                      │
└─────────────────────────────────────────────────────────┘
                          ▼
┌─────────────────────────────────────────────────────────┐
│ Select subsets of health providers from the health providers, │
│ each provider of each subset capable of treating at least one of │
│ the health needs.                                        │
│ 450                                                      │
└─────────────────────────────────────────────────────────┘
                          ▼
┌─────────────────────────────────────────────────────────┐
│ Generate, for each subset, a score based at least in part on the │
│ health provider information, the patient information, and the │
│ health guidelines.                                       │
│ 460                                                      │
└─────────────────────────────────────────────────────────┘
                          ▼
┌─────────────────────────────────────────────────────────┐
│ Determine a candidate subset of the subsets based at least in │
│ part on the scores.                                      │
│ 470                                                      │
└─────────────────────────────────────────────────────────┘
```

FIG. 4

CONSTRAINED OPTIMIZATION FOR PROVIDER GROUPS

BACKGROUND

1. Field of Art

This description generally relates to constrained optimization for a provider group based on input data, and particularly to optimizing a provider group using a machine learning model and iterative selection of groups.

2. Description of the Related Art

Constrained optimization has been used in the past to optimize objective functions based on input variables and constraints. Constrained optimization can be used with different types of objective functions, for example, to minimize cost functions and energy functions, or to maximize utility functions. The constraints may be hard constraints or soft constraints. A hard constraint defines a requirement that the optimization must satisfy. In contrast, violating a soft constraint does not eliminate a potential solution of the optimization, but may penalize the objective function. It is challenging and desirable to select groups of health providers that meet the needs of populations of users. Existing solutions to select provider groups require a large amount of manual work and do not optimize the providers based on the specific needs of the population.

SUMMARY

An optimization system optimizes groups of providers for a given population of users. The optimization system includes various engines such as a source interface engine, selection engine, and group score engine. The source interface engine receives information to be used in constrained optimization from server computers and stores the information in databases. The selection engine selects groups of providers from a set of all available providers. The group score engine generates a score for each group of providers. The selection engine continues to iteratively select groups of providers to minimize the generated score. The selection engine can use hard constraints, for example, requiring that a certain type of provider be included in all selected groups, or soft constraints, for example, requiring that a certain number of providers be included based on a size of the given population.

One example of the optimization system optimizes groups of health providers for a given population of patients. Different populations of patients may have different health needs. For example, a patient population in one state in the U.S. has more cases of depression and anxiety issues, while a patient population in another state has more cases of substance abuse. Additionally, patient populations have various treatment preferences, utilization of health provider services, and required capacities of health providers to meet their particular health needs. Thus, the optimization system uses information about a given population of patients and health guidelines to determine the health needs specific to the given population. The optimization system performs an iterative process of selecting groups of health providers—from a set of all available health providers—and generating scores for each of the groups. The score indicates how well the corresponding group of providers is able to meet the health needs of the given population. The scores may be based on weights that account for factors such as whether a health provider's office location is geographically close to many patients or whether a health provider can speak a foreign language that is commonly used in the given population. As the optimization system performs more iterations, the optimization system converges on an optimized group of health providers that best serves the health needs of the given population.

The optimization system can perform optimizations that are stochastic processes. For example, there are a large number of available health providers each associated with a multitude of characteristics such as clinical expertise, geographical location, education, demographics, etc. Additionally, there are also a large number of patients in a population each associated with different health needs, physiological conditions, demographics, medical histories, etc. Thus, the optimization system can explore a solution space during optimization, for example using machine learning, which is significantly larger than the solution space that a human user could manually analyze. The optimization system may include some level of random processes that adapt over time and converge to a solution as the optimization system learns which types of health providers match well with particular patients in a population.

In one embodiment, the optimization system receives patient information describing patients. The optimization system receives health guidelines that describe requirements for forming a provider group to treat health needs of the patients. The optimization system identifies a patient population based on the patient information and the health guidelines. The optimization system receives health provider information describing health providers. The optimization system selects subsets of health providers, where each of the selected health providers can treat one of the health needs of the patient population. The optimization system generates a score for each of the subsets using a model trained based on the received information. The score indicates how well the subset of health providers is capable of treating the health needs of the patient population. In some embodiments, a lower score indicates that a subset of health providers is more capable of treating the health needs, and thus the subset is more favorable. Based on the scores, the optimization system determines a candidate subset, for example, the subset with the lowest score among all the subsets. The optimization system can continue selecting subsets of health providers and generating scores for the subsets until the selected subsets of health providers reach a steady state or times out. The optimization system determines that a subset with the steady state value score is an optimized subset of health providers for the patient population.

BRIEF DESCRIPTION OF DRAWINGS

Figure (FIG. 1 is a block diagram of a system environment for optimizing health provider groups for patient populations according to one embodiment.

FIG. 4 is a flowchart illustrating a process for optimizing health provider groups for a patient population according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. System Overview

Figure 1:
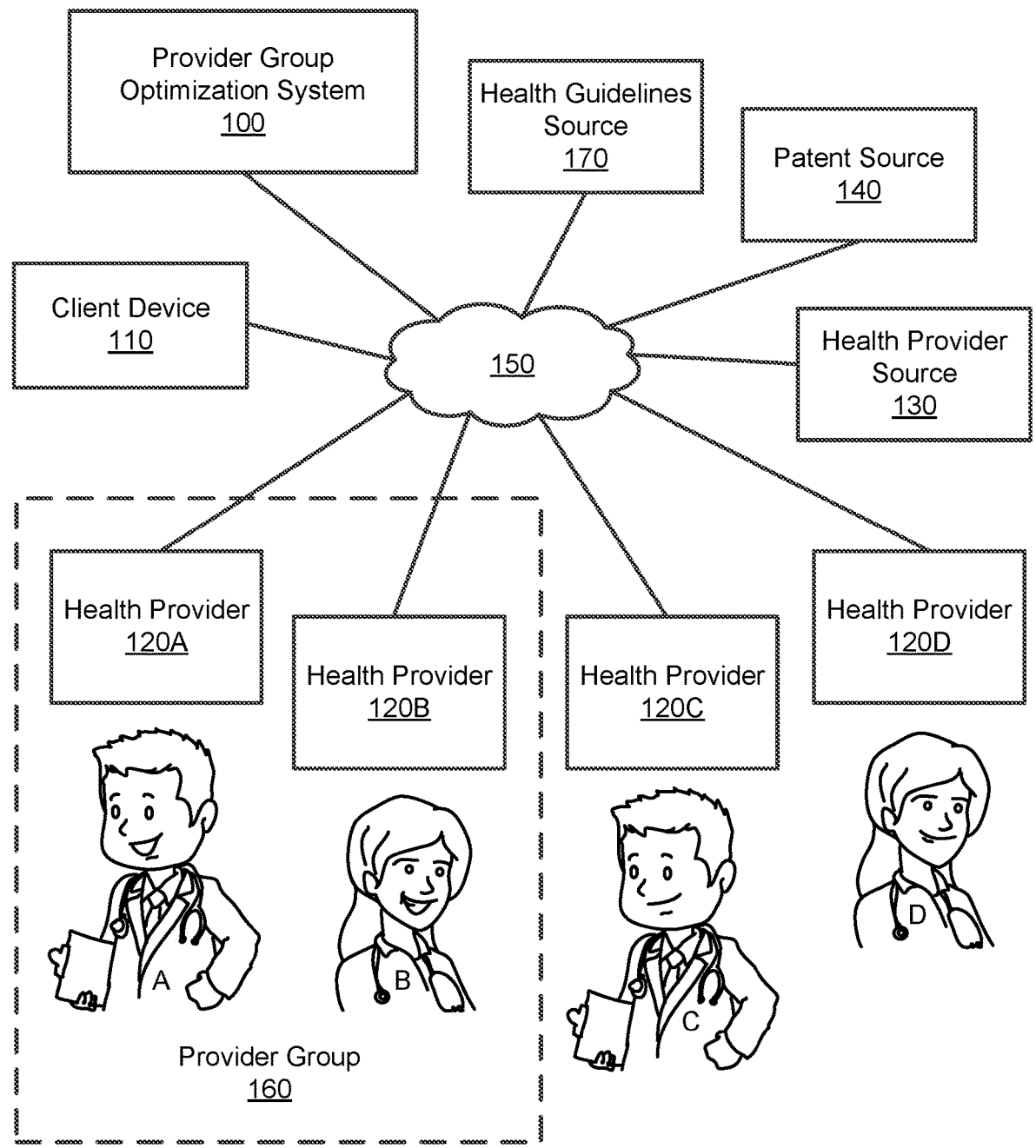

FIG. 1 is a block diagram of a system environment for optimizing health provider groups (also referred to as "provider groups") for patient populations according to one embodiment. The system environment includes a provider group optimization system 100 (also referred to as the "optimization system"), client device 110, health providers 120A, 120B, 120C, and 120D, health provider source 130, population source 140, and health guidelines source 170 connected to each other over a network 150. Health providers may also be referred to as "providers", and can include physicians, primary care physicians, hospitals, medical labs, therapists, psychiatrists, mental health specialists, behavioral health specialists, other types of health specialists, and other types of providers of health care or related services. Patients may also be referred to as users. In other embodiments, different and/or additional entities can be included in the system environment.

The client device 110 is a computing device capable of receiving user input as well as transmitting and/or receiving data via the network 150. In one embodiment, a client device 110 is a conventional computer system, such as a desktop or laptop computer. Alternatively, a client device 110 may be a device having computer functionality, such as a personal digital assistant (PDA), a mobile telephone, a smartphone or another suitable device. A client device 110 is configured to communicate via the network 150. In one embodiment, a client device 110 executes an application allowing a user of the client device 110 to interact with the optimization system 100. For example, a client device 110 executes a browser application to enable interaction between the client device 110 and the optimization system 100 via the network 150. In another embodiment, a client device 110 interacts with the optimization system 100 through an application programming interface (API) running on a native operating system of the client device 110, such as IOS® or ANDROID™.

The health provider source 130 is a computer server including one or more databases storing information about providers (e.g., PSYCHOLOGYTODAY, GOODTHERAPY®, HEALTHGRADES®, National Provider Identifier (NPI) provided by National Plan & Provider Enumeration System (NPPES), and ZOCDOC'), U.S. physician prescribing data (i.e., drugs prescription) provided by First DataBank, Medicare Part D and IMS HEALTH™, patient statistics and evidence-based treatments (e.g., provided by online resources such as UPTODATE®, SK&A, LEXISNEXIS®, and web crawling), and personal websites of therapists. The information about providers may include the provider's preferred therapies, preferred medications, target clients, conditions treated, geographical location, contact information, medical experience, training, availability, languages spoken, etc. A profile associated with a provider on the databases may include a link to a personal website of the provider. The health provider source 130 may be associated with a health maintenance organization (HMO), preferred provider organization (PPO), health insurance plan, healthcare facility, or any other type of organization for health care.

The patient source 140 is a computer server including one or more databases storing information about patients. The information can include the patients' health needs, demographics, socioeconomic status, geographical locations, and medical history. Some patients with health needs may not necessarily be actively or currently seeking treatment for their health needs. Other patients may not necessarily have a health need at a given period of time. Similar to the health provider source 130, the patient source 140 may be associated with a HMO, PPO, health insurance plan, healthcare facility, or any other type of organization for health care.

The health guidelines source 170 is a computer server including one or more databases storing health guidelines (which may also be referred to as guidelines) about filling the health needs of patients. For example, a health guideline indicates that for a population of a given size, a provider group should include providers that have the experience to treat a variety of health needs. In particular, a health guideline may indicate that for every 2000 patients of a population, there should be one primary care physician in the corresponding provider group. The health guidelines source 170 may also include medical practice standards (e.g., prescribing health guidelines of consensus practice recommendations for different treatments and medication for different medical conditions). The health guidelines source 170 may also be associated with health care laws and regulations such as the Patient Protection and Affordable Care Act (ACA) or the Health Insurance Portability and Accountability Act (HIPAA). For example, a health guideline may be based on network adequacy rules of the ACA, e.g., a provider group of a health insurance plan must ensure that patients have sufficient choice and geographical access to providers, or that a provider group must have a certain ethnic composition of providers or linguistic services.

The network 150 includes any combination of local area and/or wide area networks, using both wired and/or wireless communication systems. In one embodiment, the network 150 uses standard communications technologies and/or protocols. For example, the network 150 includes communication links using technologies such as Ethernet, 802.11, worldwide interoperability for microwave access (WiMAX), 3G, 4G, code division multiple access (CDMA), digital subscriber line (DSL), etc. Examples of networking protocols used for communicating via the network 150 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 150 may be represented using any suitable format, such as hypertext markup language (HTML) or extensible markup language (XML). In some embodiments, all or some of the communication links of the network 150 may be encrypted using any suitable technique or techniques.

The optimization system 100 is a computer server that performs constrained optimization by optimizing provider groups to serve a patient population. In particular, the optimization system 100 receives information about patients from the patient source 140 and identifies a population of patients. The optimization system 100 receives information about providers, e.g., health providers 120A, 120B, 120C, and 120D, from the health provider source 130. Based on the received information from both sources, the optimization system 100 determines an optimized group of providers that matches the health needs of the population of patients. Further, the optimization system 100 may use hard and/or soft constraints based on the received information. In the example shown in FIG. 1, the optimization system 100 determines that health providers 120A and 120B are in the optimized provider group 160, while health providers 120C and 120D are not. The optimization system 100 provides information about the group of providers to the client device 110. Though FIG. 1 shows only four providers, it should be noted that in practice, the optimization system 100 determines groups of providers including many more providers, e.g., hundreds to thousands of providers. In one embodiment, optimization system 100 identifies populations of patients based on geographical location, e.g., a first population is located in California and a second population is located in New York. In some embodiments, the optimization system 100 identifies populations of patients based on other factors, e.g., socioeconomic class or demographic information. Additionally, the information about patients from the patient source 140 may have a pre-identified population of patients, e.g., associated with a health insurance plan.

II. Provider Group Optimization System

Figure 2:
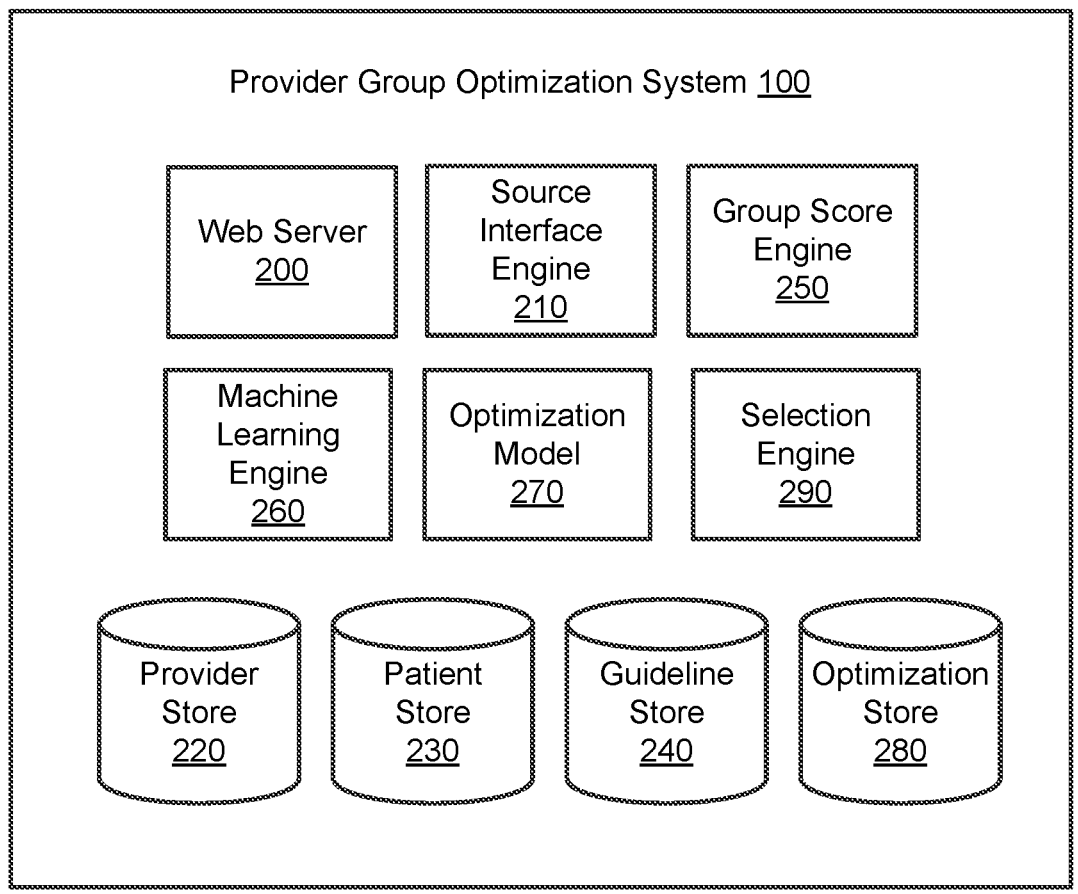
FIG. 2 is a block diagram of a provider group optimization system according to one embodiment.

FIG. 2 is a block diagram of the optimization system 100 according to one embodiment. The optimization system 100 includes a web server 200, source interface engine 210, provider store 220, patient store 230, guideline store 240, group score engine 250, machine learning engine 260, optimization model 270, optimization store 280, and selection engine 290. In other embodiments, the optimization system 100 may include additional, fewer, or different engines for various applications. Conventional components such as network interfaces, security mechanisms, load balancers, failover servers, management and network operations consoles, and the like are not shown so as to not obscure the details of the optimization system 100.

The web server 200 links the optimization system 100 via the network 150 to the client device 110, health providers 120, health provider source 130, and patient source 140. The web server 200 serves web pages, as well as other web-related content, such as web-related content in JAVA®, FLASH®, XML and so forth. The web server 200 may receive and route messages between the optimization system 100 and the client device 110, for example, instant messages, queued messages (e.g., email), text messages, short message service (SMS) messages, or messages sent using any other suitable messaging technique. The client device 110 may send a request to the web server 200 to upload information to the optimization system 100 or download information from the optimization system 100. Additionally, the web server 200 may provide application programming interface (API) functionality to send data directly to native client device operating systems, such as IOS®, ANDROID™, WEBOS® or RIM®.

The source interface engine 210 receives information from sources accessible to the optimization system 100 and stores the received information in the optimization system 100. In particular, the source interface engine 210 receives provider information from the health provider source 130 and stores the provider information in the provider store 220. Further, the source interface engine 210 receives patient information from the patient source 140 and stores the patient information in the patient store 230. Additionally, the source interface engine 210 receives health guidelines from the health guidelines source 170 and stores the health guidelines in the guideline store 240.

Provider information can describe a provider's preferred therapies (e.g., evidence based therapies or traditional therapies of a certain ethnic culture), preferred medications (e.g., sleep aid drugs or anti-depressant medications), target clients (e.g., elders, minors, or young adults), health needs treated, geographical location (e.g., hospital or office addresses), contact information (e.g., phone numbers or emails), medical experience (areas of focus, years of professional work experience, or work performance history), training (e.g., degrees earned, schools attended, or certifications), availability (capability to take new patients, office hours on weekdays and weekends, availability for phone, or online consultations), languages spoken (e.g., English, Chinese, or Spanish), etc. The health needs can describe behavioral health conditions, mental health conditions, social issues, chronic illnesses, conditions requiring medical treatment such as surgery, intervention, prescription medications, and other types of health conditions.

Patient information can describe patients' health needs (corresponding to the health needs treated by the providers described above), demographics (e.g., age, gender, race, ethnicity, languages spoken), socioeconomic status (e.g., working class or receiving government assisted benefits), geographical locations (e.g., home or work addresses), or medical history (e.g., previously diagnosed health needs, previous treatments and medications taken, or health insurance information). Additionally, the patient information can indicate an expected utilization of providers by patients, a prevalence of health needs or conditions among the patients, treatment preferences of the patients, or a capacity of providers required to meet the health needs of the patients. The prevalence of certain health needs or conditions may be based on historical data (e.g., medical records) of the patients. For example, a specific ethnic demographic of patients is more prone to being diagnosed with a particular type of genetic disease. As another example, a population of patients in a geographic area may be more likely to transmit a certain disease, e.g., patients in areas with tropical weather have a higher risk of becoming infected by diseases carried by mosquitos.

The health guidelines describe requirements for forming a provider group to treat the health needs of a given population of patients. The requirements may have varying levels of importance, e.g., optional requirements or critical requirements. For example, a health guideline indicates that each provider group should include at least one (or any other threshold value) provider who is specialized to treat patients who are minors and are suffering from depression. The corresponding population of patients does not necessarily need to currently include any minors who have depression, because a minor of the population may develop depression at a later time. As another example, a health guideline indicates that each provider group should include at least a threshold number of providers capable of taking on new patients. Further, health guidelines can indicate quotas or ratios of certain types of providers. For example, for every 1000 patients in a population, the provider group should include a therapist specialized in treating substance abuse.

As another example, a health guideline indicates that a provider group is required to have at least a threshold number of Essential Community Providers (ECP) that are specialized to serve low income and medically underserved communities.

The group score engine 250 generates scores indicating how well provider groups meet the health needs of a population of patients. In particular, the group score engine 250 takes, as input, information about the provider group, e.g., health needs served by the providers, and information about the population of patients, e.g., their aggregate health needs. The group score engine 250 outputs a score based on the input information. Typically, the score is represented by a numeric value, where a lower score indicates that most—or close to all—of the health needs of the population of patients can be provided by the provider group. In contrast, a higher score indicates that many of the health needs have less support from the provider group. The group score engine 250 can also use weights (e.g., generated by the optimization model 270 or retrieved from the optimization store 280) to generate scores, which is further described below.

In one embodiment, the group score engine 250 can use an objective function $f(group)$ to generate scores, where group represents a given group of providers:

$$f(group) = \frac{group\_size}{\sum_{i=1}^{N} (capacity\_filled_i * weight_i)}$$

The number of providers in the group is represented by parameter group_size, and the number of different types of health needs of a population of patients is represented by parameter N. The group score engine 250 determines, for each of the different types of health needs, $capacity\_filled_i$, which represents how well providers from the given provider group fill the capacity (i.e., target number of health providers) of the corresponding type of health need. For example, the population of patients requires a total capacity of ten providers who are relationship counselors. If the given provider group has eight available relationship counselors, then the group score engine 250 determines the capacity_filled$_i$ as 8/10 or 0.8, which is the ratio of the available providers of the need for relationship counselors to the total number of providers required for such need. The group score engine 250 calculates the sum of each capacity_filled$_i$ to generate a score for the given provider group.

In some embodiments, the group score engine 250 applies the varying weights, weight generated by the optimization model 270, to at least one of the capacity_filled$_i$. In one embodiment, weights are represented by a percentage or a decimal value from 0 to 1, inclusive. A weight associated with an identified health need indicates severity or importance of the identified health need among the health needs associated with the patient population. In one embodiment, the weights are generated by the optimization model 270 such that the output of objective function $f(group)$ is minimized. Thus, in embodiments using the objective function $f(group)$, a higher weight results in a lower score for a given group of providers, which is more desirable to meet the health care needs of the identified patient population. Though only one weight is shown in the objection function, it should be noted that the group score engine 250 can use multiple weights, e.g., a first weight to account for the geographical location of providers and a second weight to account for health specialties of providers. Since capacity_filled$_i$ is determined based on health needs only, the group score engine 250 applies weights to account for other factors (e.g., geographical distribution of providers or availability of providers to take new patients) when generating scores.

In some embodiments, the optimization system 100 uses the weights generated by the group score engine 250 as soft constraints. In particular, the objective function is penalized (e.g., because the resulting score is greater) if the optimization system 100 selects a group of providers that do not sufficiently satisfy health needs associated with heavier weights. The optimization system 100 may use soft constraints based on optional requirements (described by the health guidelines) to optimize the objective function. Further, the optimization system 100 may use hard constraints based on critical requirements (described by the health guidelines).

The machine learning engine 260 trains the optimization model 270 using features based on provider information, patient information, and health guidelines. The machine learning engine 260 can retrieve information from the provider store 220, patient store 230, and guideline store 240 to extract features. In addition, the machine learning engine 260 can receive predetermined features from any other source accessible to the optimization system 100. The features indicate, for example, types of health needs that are more critical or prevalent in patients, health services that patients frequently utilize, common preferences of patients, characteristics of high quality providers (e.g., providers who have multiple specialties, use evidence-based treatment methodologies, or have positive patient reviews), geographical areas with denser populations of patients, or times during the day or week that patients are typically available to see a provider, among other types of features. The machine learning engine 260 can periodically re-train the optimization model 270 using features based on newly received information, e.g., information about new providers who have joined a set of available providers. For example, the machine learning engine 260 can train the optimization model 270 using machine learning techniques including linear regression, decision trees, support vector machines, classifiers (e.g., a Naive Bayes classifier), and gradient boosting.

The optimization model 270 is trained by the machine learning engine 260 to generate weights used in the objective function $f(group)$ described above based on input provider information, patient information, and health guidelines. In one embodiment, the weights are generated by the optimization model 270 such that the output of the objective function $f(group)$ is minimized. The optimization model 270 can store the generated weights in the optimization store 280. The weights may apply to specific providers (e.g., a first provider is weighed more heavily than a second provider) or to specific types of health needs (e.g., providers who treat suicide are weighed more heavily than providers who treat eating disorders). In some embodiments, the optimization model 270 receives predetermined weights from a source outside of the optimization system 100. For example, the predetermined weight for providers who treat suicide is 0.4, while the predetermined weight for providers who treat eating disorders is 0.2.

In embodiments using the objective function $f(group)$, the optimization model 270 generates greater weights—compared to the average provider of a set of providers—for providers with certain desired qualities such as more professional experience, speak multiple languages, meet a certain cultural or social preference, have more availability, or are more accessible to a large portion of patients in a population. For example, a provider with more years of professional experience has developed more specialty areas, e.g., the provider can treat patients with depression, substance abuse, relationship issues, and post-traumatic stress disorder (PTSD). A provider who can speak multiple languages is able to (without having to use a translator) treat patients of ethnic minorities who may not necessarily know how to speak or understand English fluently. A provider who has experience with different cultural or social sensitivities can treat a more diverse range of patients such as lesbian, gay, bisexual, and transgender (LGBT) patients or patients who prefer traditional Chinese treatments (e.g., herbal medicine or acupuncture). A provider who can admit new patients is advantageous for patients in a population who want to change or find new providers. A provider with flexible evening and weekend office hours is desirable for patients who are busy during regular business hours. A provider who can schedule appointments promptly (e.g., within 10 business days or less from a request) is desirable for patients who have more urgent health needs. A first provider who is located in an urban or suburban area or located nearby public transportation (e.g., bus or train stations) is more accessible to patients than a second provider located in a rural area. In other words, the average geographical distance (or travel time) from the patients to the first provider is less than the average geographical distance from the patients to the second provider. Providers with the desired qualities described above are more likely to be able to serve a greater number of patients of a given population. Thus, a provider group including these providers should have a lower score.

As the machine learning engine 260 trains the optimization model 270 over time, the optimization model 270 learns which types of providers are more likely to meet the health needs of populations of patients. The optimization model 270 thus generates weights that provide additional granularity in evaluating a provider group. For example, the weights help distinguish provider groups that only meet the different types of health needs of a population from provider groups that both meet the different types of health needs and also are geographically distributed among the population to improve the patients' accessibility to providers. Thus, the group score engine 250 can uses the weights to generate scores that accurately indicate how well a provider group meets the health needs of a given patient population.

The selection engine 290 selects an optimized group of providers from a set of available providers through one or more iterations. A group of providers can include locked providers from a locked set and unlocked providers from an unlocked set. The locked set is initially an empty set and the unlocked set initially includes all available providers. In one embodiment, the selection engine 290 moves a provider from the unlocked set to the locked set when the provider signs up with the provider group optimization system 100 or an insurance plan. In other embodiments, the selection engine 290 moves known high quality providers (e.g., based on information from the provider store 220) from the unlocked set to the locked set. The optimized provider group is capable of treating health needs of a given patient population. In particular, the selection engine 290 selects a first provider group using providers from the locked set and the unlocked set. The selection engine 290 must include locked providers in any selected provider group, e.g., because providers of the locked providers are already included in an insurance plan (e.g., a HMO or PPO), are high quality providers, or previously signed up with the provider group optimization system 100. In contrast, the selection engine 290 may or may not choose to include some of the unlocked providers. Thus, the selection engine 290 uses the locked providers as a hard constraint to optimize the objective function.

The selection engine 290 provides the first provider group to the group score engine 250, which generates a first score for the initial provider group. The selection engine 290 selects a second provider group from the set of available providers. The selection engine 290 provides the second provider group to the group score engine 250, which generates second a score for the second provider group. The selection engine 290 selects a third provider group from the set based on the first two provider groups and corresponding scores. For example, the first score is lower than the second score, e.g., indicating that the first provider group is better matched to the health needs of the given population, relative to the second provider group. Thus, the selection engine 290 selects more providers from the first provider group than the second provider group to include in the third provider group. The selection engine 290 can repeat this selection and score comparison process many times (e.g., hundreds to thousands of iterations). Accordingly, over time with iterations, the selection engine 290 determines which providers—when selected into provider groups—are associated with lower scores (e.g., more desirable to be selected into a provider group). After completed all iterations of the process, the selection engine 290 determines a provider group that has been optimized, e.g., associated with the lowest scores among all the provider groups formed. In some embodiments, the selection engine 290 requires less iteration to determine the optimized provider group if the optimization model 270 has been trained to generate weights (used by the group score engine 250) that accurately account for the different characteristics of providers, as previously described. Less iteration is advantageous because it reduces the time and processing power required for the selection engine 290.

III. Process for Optimizing Provider Groups

FIG. 4 is a flowchart illustrating a process 400 for optimizing health provider groups for a patient population according to one embodiment. In some embodiments, the process 400 is used by the optimization system 100—e.g., engines of the optimization system 100 described with reference to FIG. 2—within the system environment in FIG. 1. The process 400 may include different or additional steps than those described in conjunction with FIG. 4 in some embodiments or perform steps in different orders than the order described in conjunction with FIG. 4. The steps of the process 400 are described below in an example use case with reference to FIGS. 3A-F.

The source interface engine 210 receives 410 patient information from the patient source 140 to identify a patient population. The patient information describes a set of patients, e.g., the number of patients located in a certain geographical region, the demographics of the patients, etc.

Figure 3A:
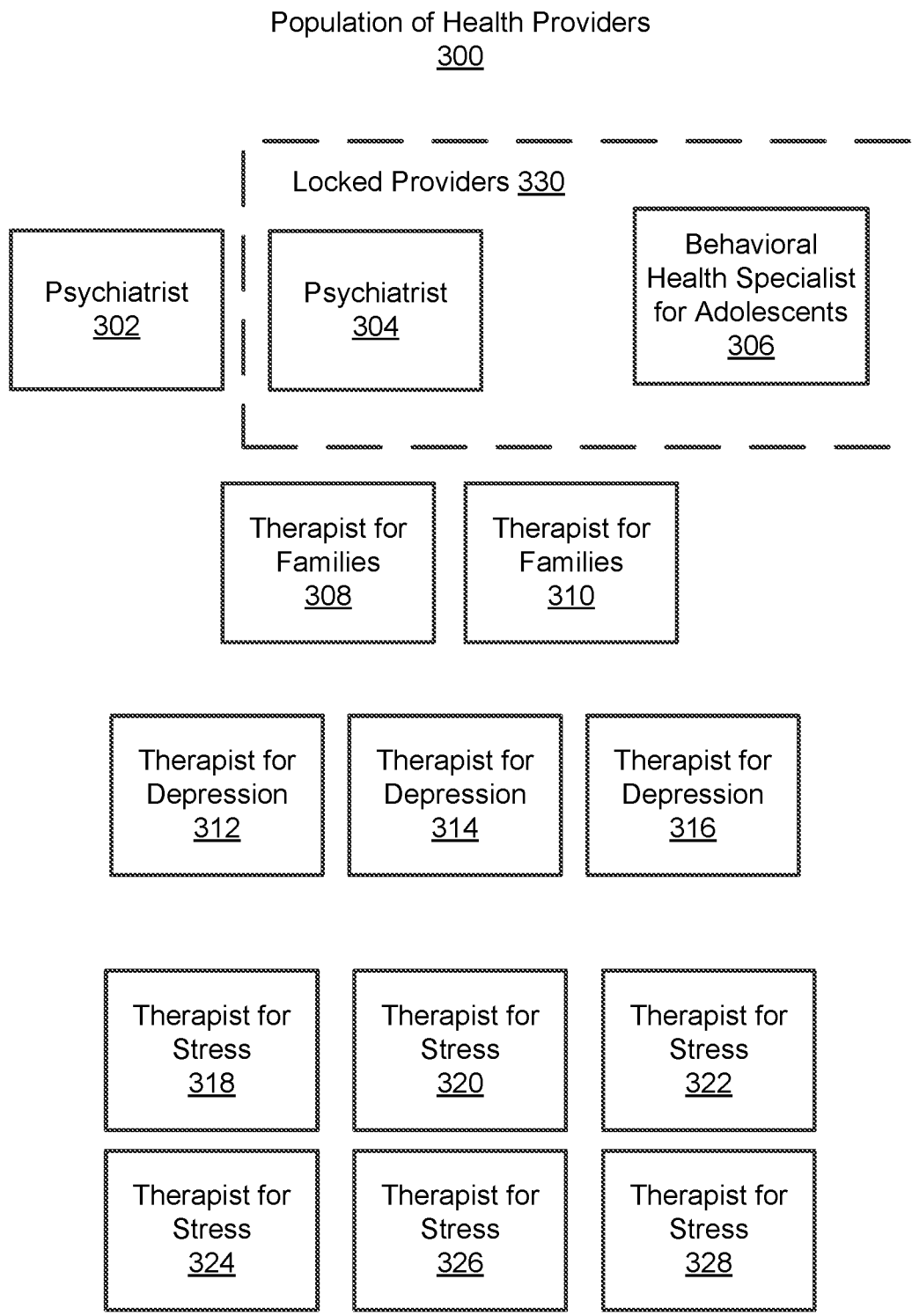
FIG. 3A is a diagram of a set of health providers according to one embodiment.

FIG. 3A is a diagram of a set 300 of health providers according to one embodiment. The set 300 includes two psychiatrists 302 and 304, one behavioral health specialist for adolescents 306, two therapists for families 308 and 310, three therapists for depression 312, 314, and 316, six therapists for stress 318, 320, 322, 324, 326, and 328. Locked providers 330 is initialized to include high quality providers known to the optimization system, e.g., the psychiatrist 304 and behavioral health specialist for adolescents 306. In one embodiment, sets of providers represent all of the providers who are located in a particular geographic region, e.g., one of set of providers represents the providers in the San Francisco County in California and another set of providers in the Santa Clara County. In other embodiments, the set 300 of providers may include any number or other types of providers, e.g., providers specialized to treat autism or attention deficit disorder (ADD). Further, in other embodiments, the locked providers 330 may include any number of providers or other types of providers.

The source interface engine 210 receives 420 health guidelines describing requirements for forming a provider group to treat health needs of the set of patients, from the health guideline source 170. The selection engine 290 identifies 430 a patient population based on the patient information and the health guidelines. The identified patient population has health needs. Based on the patient information, the health guidelines indicate that the identified patient population requires three types of providers: psychiatrists 345, providers for minors 350 (e.g., patients under 18 years old), and providers for depression and stress 355. The source interface engine 210 receives 440 health provider information from the health provider source 130. The health provider information describes characteristics of a set of providers, who are candidates to be included a group of providers for the identified patient population, and is illustrated in FIG. 3A. The selection engine 290 selects 450 two or more provider groups (i.e., subsets) of providers from the set 300 of providers shown in FIG. 3A. Each of the selected providers is capable of treating at least one of the health needs of the identified patient population, which in this example corresponds to one of the three types of providers. For example, the selection engine 290 selects the two provider groups shown in FIGS. 3B-C.

Figure 3B:
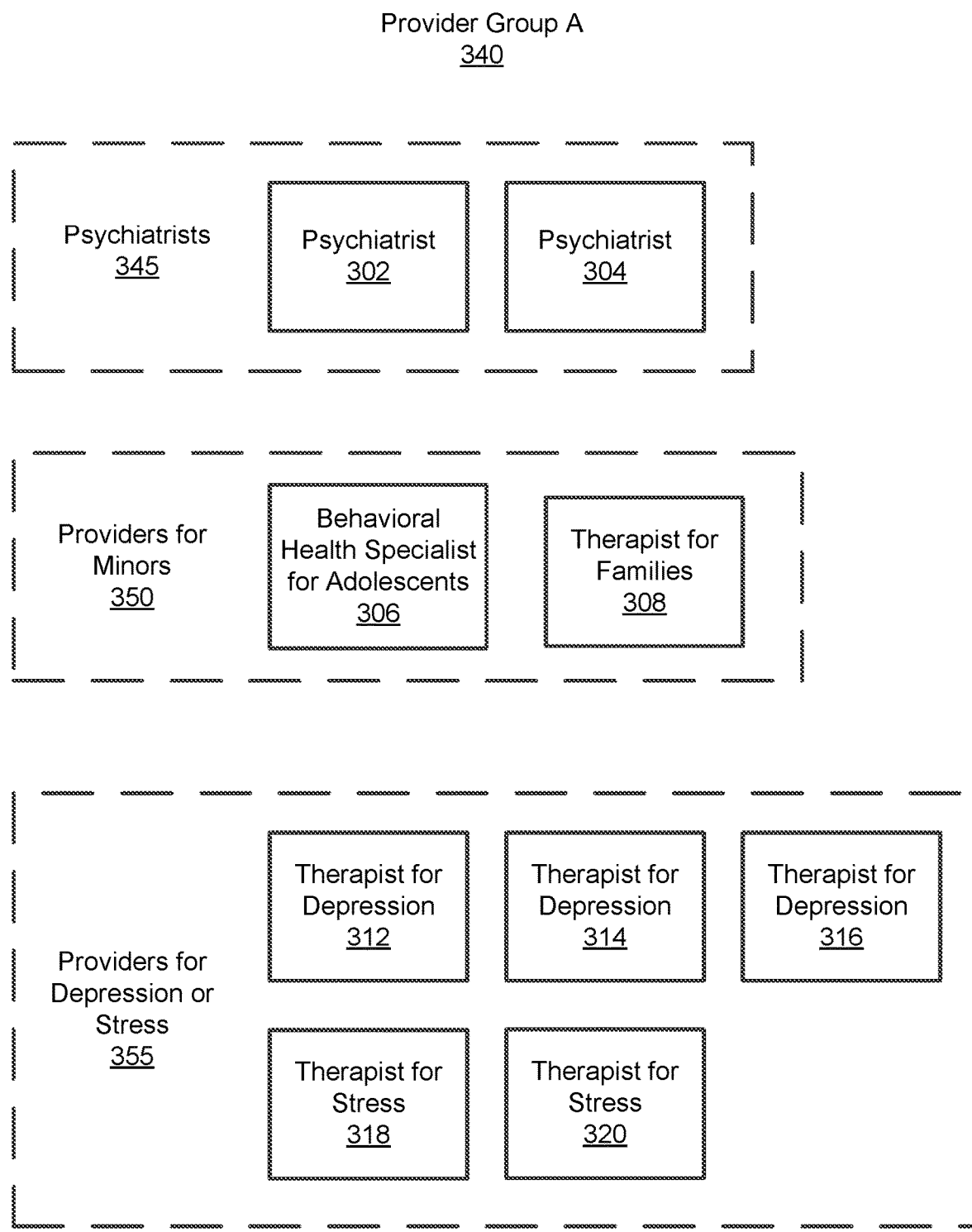
FIG. 3B is a diagram of a first provider group from the set of health providers shown in FIG. 3A according to one embodiment.

FIG. 3B is a diagram of a first provider group 340 from the set 300 of health providers shown in FIG. 3A according to one embodiment. The selection engine 290 selects the first provider group 340, also referred to as provider group A, from the set 300 shown in FIG. 3A. The selection engine 290 can select the first provider group 340 based on a best guess. For example, the selection engine 290 selects high quality providers from the set 300 based on information from the provider store 220 (e.g., providers with more years of experience treating patients or providers with positive reviews from former patients). Provider group A includes a total of nine providers, which are categorized into the three types of providers: psychiatrists 345, providers for minors 350, and providers for depression or stress 355. Though three types of providers are shown in FIG. 3B for purposes of illustration, in practice, there are many more types of providers required for a provider group. The psychiatrists 345 category includes psychiatrists 302 and 304. The providers for minors 350 category includes behavioral health specialist for adolescents 306 and therapist for families 308. The providers for depression or stress 355 category includes therapists for depression 312, 314, and 316, and therapists for stress 318 and 320. Since the psychiatrist 304 and behavioral health specialist for adolescents 306 are locked providers, the selection engine 290 automatically includes these two providers in the provider group A.

Figure 3C:
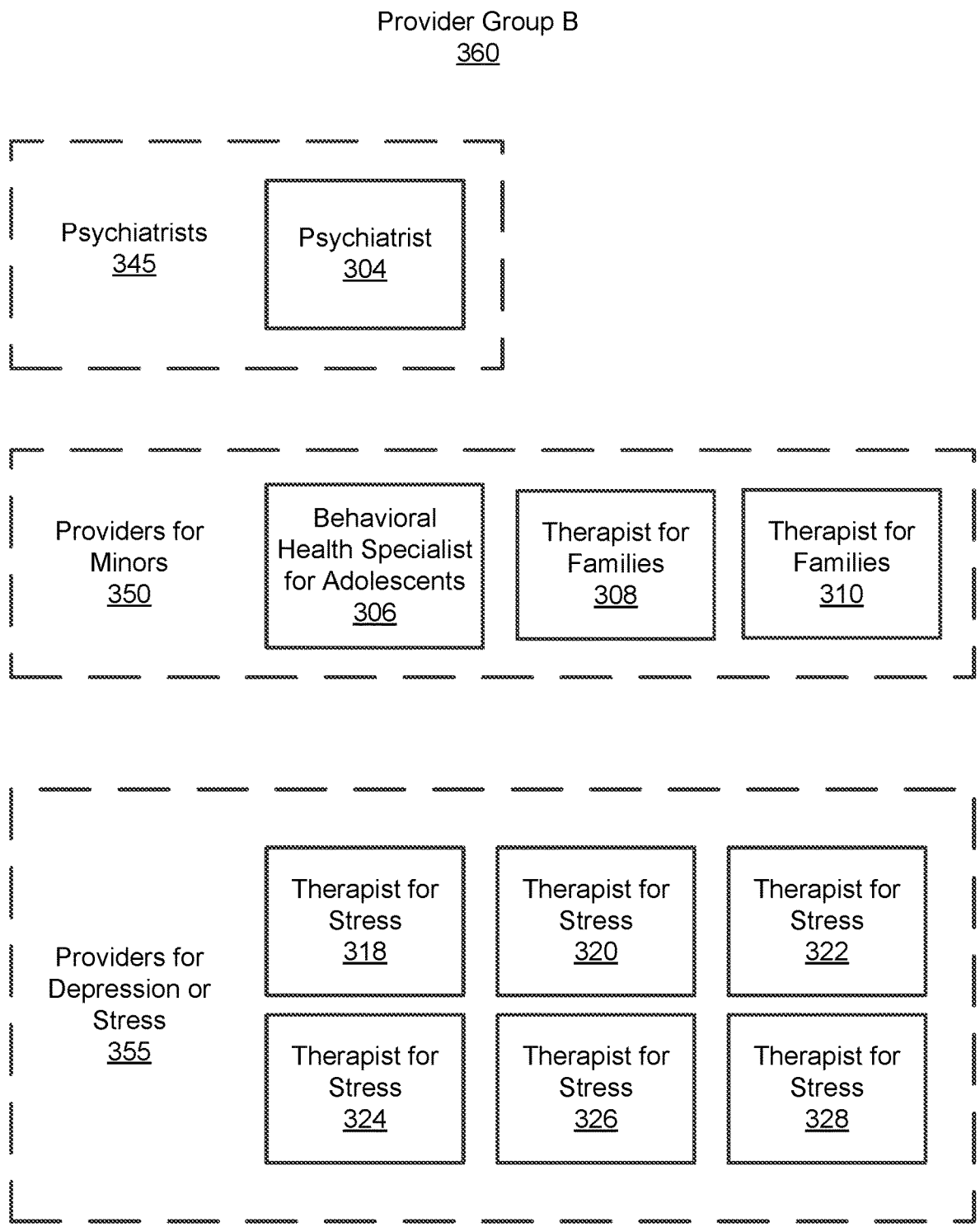
FIG. 3C is a diagram of a second provider group from the set of health providers shown in FIG. 3A according to one embodiment.

FIG. 3C is a diagram of a second provider group 360 from the set 300 of health providers shown in FIG. 3A according to one embodiment. The selection engine 290 selects the second provider group 340, also referred to as provider group B, from the set 300 shown in FIG. 3A. Provider group B includes a total of eleven providers, which are categorized into the three types of providers similarly as provider group A. The psychiatrists 345 category includes psychiatrist 304. The providers for minors 350 category includes behavioral health specialist for adolescents 306 and two therapists for families 308 and 310. The providers for depression or stress 355 category includes six therapists for stress 318, 320, 322, 324, 326, and 328. Since the psychiatrist 304 and behavioral health specialist for adolescents 306 are locked providers, the selection engine 290 automatically includes these two providers in the provider group B.

Figure 3D:
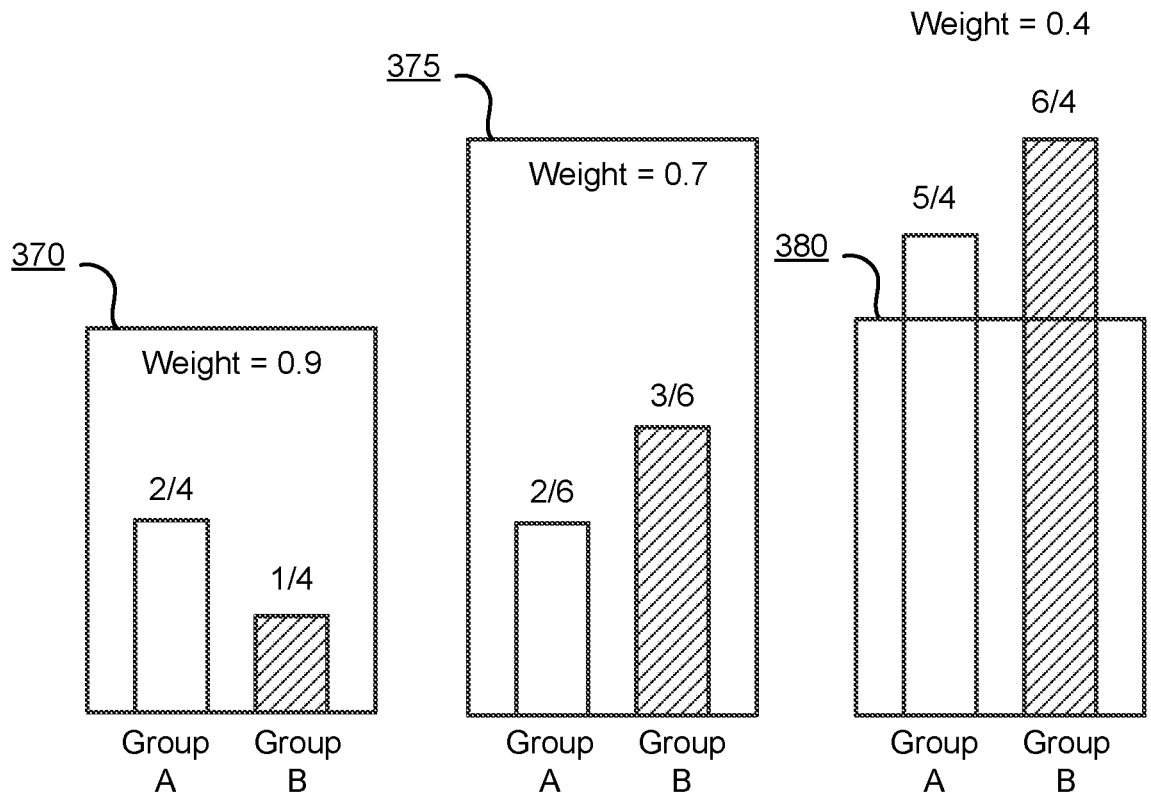
FIG. 3D is a diagram comparing the first group of providers with the second group of providers according to one embodiment.

FIG. 3D is a diagram 365 comparing the first group of providers with the second group of providers based on output of the objective function $f(group)$ associated with each group according to one embodiment. The diagram 365 includes three bar graphs 370, 375, and 380 illustrating the health needs of the identified patient population, e.g., based on health guidelines from the guideline store 240. The bar graph 370 indicates that a provider group should have four providers under the psychiatrist 345 category. The bar graph 375 indicates that the provider group should have six providers under the providers for minors 350 category. The bar graph 380 indicates that a provider group should have four providers under the provider for depression or stress 355 category. Each bar graph includes a bar corresponding to the provider group A and the provider group B based on the data shown in FIGS. B-C. For instance, provider group A includes two providers under the psychiatrist 345 category. Thus, the corresponding bar in bar graph 370 is labeled with the ratio 2/4, in other words, two providers out of the target capacity of four. The ratio may be less than, equal to, or greater than one, depending on the number of providers in a provider group and the capacity based on health guidelines.

Each bar graph (and corresponding type of health need) is associated a weight generated by the optimization model 270. In particular, the psychiatrist 345 category has a weight of 0.9, the providers for minors 350 category has a weight of 0.7, and the providers for depression or stress 355 category has a weight of 0.4. Thus, the weights indicate that the identified patient population has the strongest need for psychiatrists among the three types of providers because the weight for the psychiatrist 345 category is the greatest among the three.

The group score engine 250 generates 460, a score for each provider group using a model (e.g., the optimization model 270 shown in FIG. 2) trained based on the health provider information, patient information, and health guidelines. Each score indicates a measurement of how well the corresponding provider group is capable of treating the health needs of the identified patient population. In the embodiment shown in FIG. 3D, the group score engine 250 uses the objective function (previously described in Section II. Provider Group Optimization System) and the weights (e.g., generated by the optimization model 270) shown with the bar graphs to generate the scores. In particular, the score for provider group A is:

$$f(\text{Group A}) = 9 * \sum_{i=1}^{3} \frac{1}{\text{capacity\_filled}_i * \text{weight}_i} = \frac{9}{0.9*2/4 + 0.7*2/6 + 0.4*5/4} \approx 7.6$$

The score for provider group B is:

$$f(\text{Group B}) = \frac{10}{0.9*1/4 + 0.7*3/6 + 0.4*6/4} \approx 8.5$$

Since the score for provider group A is less than the score for provider group B, provider group A is better matched to serve the health needs of the identified patient population. A lower number of total providers in the provider group may be desirable to reduce undesired redundancies. For example, the health guidelines indicate that the identified patient population requires only four providers for depression or stress 355, but both provider groups exceeded the target capacity. By reducing the number of providers for depression or stress 355 down to four, the resulting score for the provider group may be lower. In addition, though provider group B included more providers than provider group A, provider group A included an additional provider in the psychiatrist 345 category than did provider group B. Since the psychiatrist 345 category was weighed the heaviest among the three categories, the psychiatrist 345 category weight contributed to reducing the score of provider group A to become less than the score of provider group B.

The selection engine 290 determines 470 a candidate provider group (which may also be referred to as a candidate subset) of the provider groups based on the generated scores. In this example, the selection engine 290 determines that provider group A is the candidate provider group between provider group A and B because provider group A has the lower score (i.e., 7.6 is less than 8.5). In some embodiments, the selection engine 290 determines the candidate provider group based on criteria in addition to the scores. For example, if a particular provider group does not satisfy a critical requirement of a health guideline, then the selection engine 290 does not include the particular provider group for consideration to be the candidate provider group, regardless of the corresponding score. Critical requirements can include, for example, requiring that the patients' average travel time (e.g., by car) to an office of a provider of the provider group is under 20 minutes, or requiring that a minimum number of providers in the provider group are available until 10 PM on at least one weekday or for at least four hours on Saturdays.

Figure 3E:
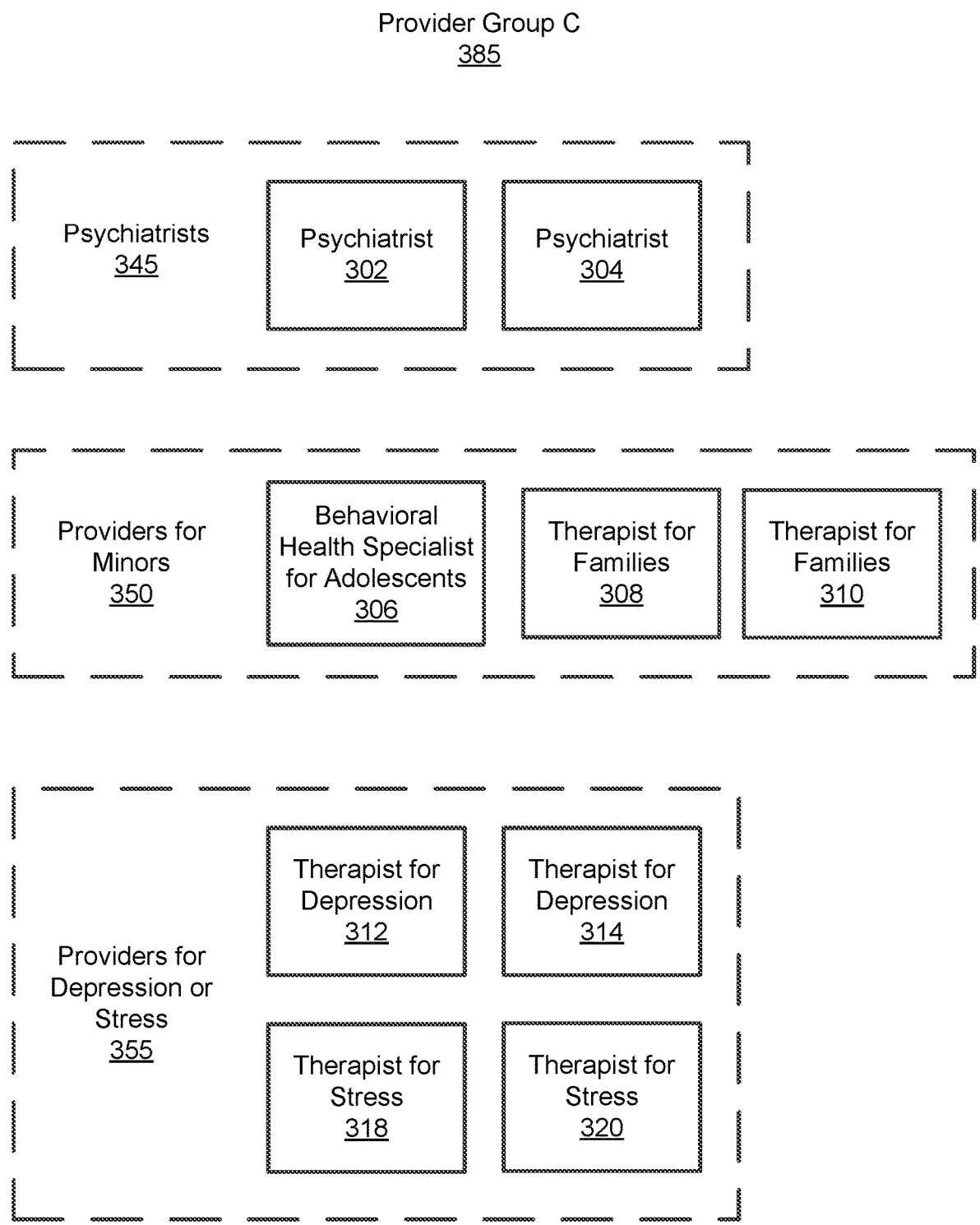
FIG. 3E is a diagram of a third provider group from the set of health providers shown in FIG. 3A according to one embodiment.
Figure 3F:
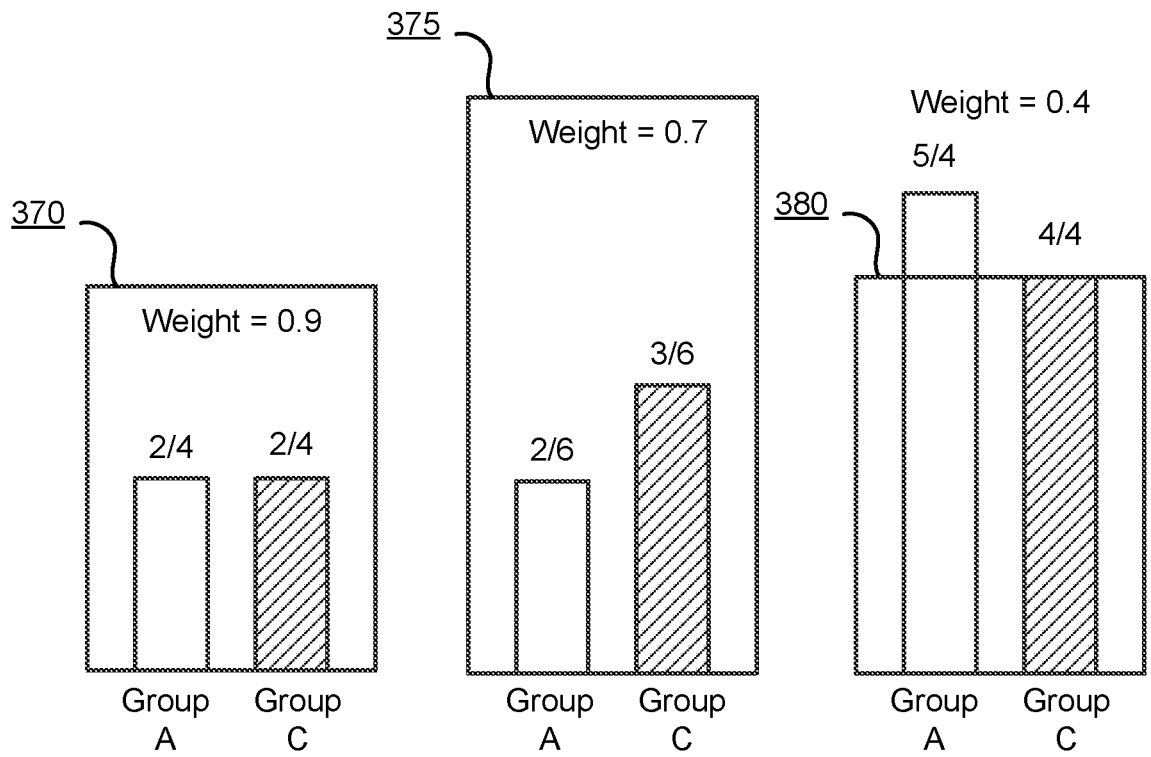
FIG. 3F is a diagram comparing the first group of providers with the third group of providers according to one embodiment.

The optimization system 100 can repeat the steps 450 to 470 of the process 400 multiple times to further optimize the candidate provider group. For example, the optimization system 100 may exchange unlocked providers between provider group A and provider group B to improve the objective function output associated each provider group in subsequent iterations. The optimization system 100 may replace worse performing groups with new groups of providers during the iteration process. The optimization system 100 may introduce new available providers to a provider group by relaxing quality constraints on provider selections if it improves the performance of the provider group. In other words, there may be another provider group that has not been selected by the selection engine 290 and that has an improved score than the current candidate provider group. Adding providers who are categorized as psychiatrists 345 or providers for minors 350 to provider group A, or removing one of the providers under providers for depression or stress 355, would improve the score for provider group A. However, there are no more available psychiatrist 345 type providers in the set 300. FIGS. 3E-F show another iteration of the steps 450 to 470.

FIG. 3E is a diagram of a third provider group from the set 300 of health providers according to one embodiment. The selection engine 260 selects the third provider group 385, also referred to as provider group C, from the set 300 shown in FIG. 3A. Provider group C includes a total of nine providers. The psychiatrists 345 category includes psychiatrists 302 and 304. The providers for minors 350 category includes behavioral health specialist for adolescents 306 and therapists for families 308 and 310. The providers for depression or stress 355 category includes therapists for depression 312 and 314 and therapists for stress 318 and 320.

FIG. 3F is a diagram 390 comparing the first group of providers with the third group of providers according to one embodiment. The score for provider group A was previously calculated as approximately 7.6. The group score engine 250 uses the objective function and weights to generate the score for provider group C:

$$f(\text{Group C}) = \frac{9}{0.9*2/4 + 0.7*3/6 + 0.4*4/4} \approx 7.5$$

The selection engine 290 determines that provider group C is the new candidate provider group among provider groups A, B and C, because provider group C has the lowest score (i.e., 7.5 is less than 7.6 and 8.5). Generally, as the optimization system 100 performs more iterations, the score of the resulting candidate provider group will initially decrease because the optimization system 100 learns which of the available providers are best matched to the population. After a certain number of iterations, the score may reach a steady state, i.e., the score does not change or fluctuates around a certain steady state value (e.g., a predetermined steady state value). The optimization system 100 stops iterating once the steady state has been reached, and the resulting candidate provider group is considered to be the optimized candidate provider group, in other words, the provider group of the set that is best matched to serve the health needs of the population. In some embodiments, the optimization system 100 reduces the amount of constraints (e.g., critical requirements that need to be satisfied based on the health guidelines) to reach the steady state or determine a provider group with a score lower than a threshold value. In some embodiments, the optimization system 100 stops iterating after a predetermined timeout period. By timing out, the optimization system 100 can avoid iterating indefinitely in situations where similar local minima solutions exist.

The optimization system 100 provides information about the candidate or optimized provider group to the client device 110. Since the selection engine 290 can identify which providers are associated with lower scores when included in a provider group, the information can include a priority queue. The priority queue is an ordered list of these more desirable providers, for example, providers associated with the highest (e.g., top 10%) weights among all providers, or providers associated with weights greater than a threshold value. A user of the optimization system 100 (e.g., interacting with the optimization system 100 via the client device 110) can use provided information to help design provider groups, for example, for a health insurance plan or independent practice association (IPA). Based on the priority queue, the user can invite the most desirable providers identified by the optimization system 100 to join a provider group in real life.

In another use case, the user provides information about an existing provider group and population of patients to the optimization system 100. In response, the optimization system 100 provides information indicating any shortages of providers, e.g., a need for more behavioral health providers, providers who can speak a foreign language, or providers located in a certain neighborhood. Thus, the user can use the optimization system 100 to help modify existing provider groups to better serve the health needs of patients. Over time, providers available in a certain area may change, e.g., because new providers graduate from school and begin practicing, while older providers retire. Additionally, a population of patients in a certain area may change as patients move in or out of the area, or as old patients pass away and new patients are born. In some embodiments, the optimization system 100 proactively determines any shortages of providers in an existing provider group. The optimization system 100 may autonomously perform optimization of the existing provider group without requiring any manual input from a user. Thus, the optimization system 100 can flag shortages of necessary providers in advance, for example, determining that the existing provider group does not include a recommended three autism specialists to treat a given population.

The optimization system 100 can retrieve information about existing provider groups and existing populations of patients and update the existing provider groups in response to changes in the available providers and/or the existing population of patients. For example, optimization system 100 can identify providers from a pool of available providers to add to an existing provider group, or identify providers to remove from the existing provider group. In one embodiment, the optimization system 100 uses scores generated by the group score engine 250 to determine whether to add or remove providers from an existing provider group. For instance, if including a new provider to an existing provider group results in a lower score for the updated provider group, then the optimization system 100 adds the new provider to the existing provider group.

Health insurance plans are often associated with a group of health providers. Typically, the group includes primary care physicians as well as providers who are specialized to treat a variety of health needs including behavioral health conditions, medical conditions, and social issues. Patients who are insured under the health insurance plan may seek treatment for their health needs from the health providers in the group. Patients with an insurance plan usually need to pay more money—in addition to the regular premiums that they pay to have the insurance plan—to seek treatment from health providers outside of their group. Thus, it is desirable and challenging to identify a patient population with varying health needs and to ensure that the provider group for that patient population includes a sufficient number and range of high quality health providers capable of treating the health needs of the patient population.

Existing health insurance plans may use "narrow networks" to lower insurance premiums for patients. These plans establish certain criteria or quality standards that the health providers in the group must satisfy. However, a downside of these plans is that since the group has fewer health providers, patients have fewer health providers to choose from. Other existing health insurance plans may use "tiered networks" that have different levels of premium payments depending on different tiers of health providers. For instance, the patient has to pay more to seek treatment from a health provider who is categorized under a high quality tier. However, the tiers introduce complexity that can confuse both patients and health providers. Additionally, it may be difficult to accurately organize health providers into the appropriate tier.

Determining provider groups that are well matched to the health needs of certain populations of patients can help reduce health insurance premiums for patients and reduce complexity of health insurance plans. In particular, the optimization system 100 helps identify providers that are not well matched to the population's health needs. Since these providers are not included (or removed from) a provider group, the overall quality of the provider group is improved. Thus, patients do not have to search through providers that are not likely a good match to find a provider who is suitable to their particular health needs and is conveniently accessible. Further, the optimization system 100 identifies redundancies where there are too many providers of a certain type (e.g., providers for the elderly or for babies) in a provider group. Generally, a provider group with fewer providers is less expensive for an administrator of the provider group to maintain. Accordingly, the administrator can charge a lower premium for patients to join a health insurance plan associated with the provider group.

IV. General

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A system for constrained optimization of groups of health providers, comprising:

a source interface engine configured to receive information from a plurality of server computers and store the information in a database, the information including:
user information about the plurality of users,
health guidelines including requirements for filling certain health needs of patients or including a medical practice standard and describing one or more constraints to be satisfied for forming a provider group to treat a plurality of health needs of a plurality of users, the one or more constraints including a hard constraint that must be satisfied and a soft constraint that may be satisfied, and
provider information describing a plurality of health providers;
a selection engine configured to select a plurality of subsets of health providers from the plurality of health providers according to at least one of the hard constraint or the soft constraint, each health provider of each subset capable of treating at least one of the health needs of the plurality of users, the hard constraint requiring a particular type of health provider be included in all subsets of the plurality of subsets, and the soft constraint requiring a particular number of health provider be included based on a size of a user population;
a first machine learning model configured to receive input capabilities of each of the plurality of health providers, and output a respective weight for each respective health provider of the plurality of health providers; and
a group score engine configured to generate, for each subset of health providers of the plurality of subsets, a score using a second machine learning model trained based on the guidelines, the score indicating a measurement of a capability of the subset of health providers for treating the plurality of health needs, the score being determined at least in part based on the respective weights for each respective health provider in each respective subset of health providers;
the selection engine being further configured to determine a candidate subset from the plurality of subsets using the scores.

2. The system of claim 1, wherein the candidate subset has the lowest score among all subsets of the plurality of subsets.

3. The system of claim 1, wherein the guidelines indicate that a number of health providers of the plurality of health providers capable of treating new users from the plurality of users is greater than a threshold value for the user population.

4. The system of claim 1, wherein the guidelines indicate that a number of health providers of the plurality of health providers capable of treating a certain health need of the plurality of health needs is greater than a threshold value for the user population.

5. The system of claim 1, wherein the selection engine is further configured to, for each subset of the plurality of subsets:
determine, for each of the plurality of health needs:
a target number of health providers to treat the health need,
a number of health providers of the subset capable of treating the health need, and
a ratio of the number of health providers capable of treating the health need to the target number of health providers;
wherein the score is based on a sum of each of the ratios and a total number of health providers in the subset.

6. The system of claim 5, wherein the group score engine is further configured to:
minimize the score for the corresponding subset of health providers based on the sum of the weighted ratios and the total number of health providers in the corresponding subset.

7. The system of claim 1, wherein the selection engine is further configured to:
compare the scores associated with the plurality of subsets of health providers; and
select the subset having the lowest score as the candidate subset of health providers.

8. The system of claim 1, wherein the selection engine is further configured to:
exchange a selected numbers of health providers included in one subset with another subset of the plurality of subsets;
wherein the group score engine is configured to recalculate the scores associated with the plurality of subsets in response to the exchange of the selected number of health providers; and
wherein the selection engine is further configured to select a subset as the candidate subset based on the recalculated scores associated with the plurality of subsets.

9. The system of claim 1, wherein the plurality of health providers includes at least one locked health provider, the at least one locked health provider being initially selected from a set of health providers known to provide high quality health care services, and wherein each subset of health providers includes each of the locked health providers.

10. The system of claim 1, wherein the selection engine is further configured to iteratively select pluralities of subsets of health providers from the plurality of health providers and generate scores for each of the subsets until the lowest score of a subset among all subsets reaches a predetermined steady state value.

11. The system of claim 1, wherein the selection engine is further configured to determine one or more shortages of health providers of the candidate subset for treating the plurality of health needs based at least in part on the scores.

12. A computer program product comprising a non-transitory computer readable storage medium having instructions encoded thereon that, when executed by a processor, cause the processor to:
receive patient information describing a plurality of patients;
receive health guidelines including requirements for filling certain health needs of patients or including a medical practice standard and describing one or more constraints to be satisfied for forming a provider group to treat health needs of the plurality of patients, the one or more constraints including a hard constraint that must be satisfied and a soft constraint that may be satisfied;
identify a patient population based on the patient information and the health guidelines, the identified patient population having a plurality of health needs;
receive health provider information describing a plurality of health providers;
select a plurality of subsets of health providers from the plurality of health providers according to at least one of the hard constraint or the soft constraint, each provider of each subset capable of treating at least one of the health needs of the identified patient population, the hard constraint requiring a particular type of health provider be included in all subsets of the plurality of subsets, and the soft constraint requiring a particular number of health provider be included based on a size of a user population;

input capabilities of each of the plurality of health providers into a first machine learning model;

receive, as output from the first machine learning model, a respective weight for each respective health provider of the plurality of health providers;

generate, for each subset of health providers of the plurality of subsets, a score using a second machine learning model trained based at least in part on the patient information, the health guidelines, and the health provider information, the score indicating a measurement of a capability of the subset of health providers for treating the plurality of health needs of the identified patient population, the score being determined at least in part based on the respective weights for each respective health provider in each respective subset of health providers; and determine a candidate subset of the plurality of subsets of health providers based at least in part on the scores.

13. The non-transitory computer readable storage medium of claim 12, wherein generate, for each subset of the plurality of subsets, a score comprises:

determine, for each of the plurality of health needs of the identified patient population:
   a target number of health providers to treat the health need,
   a number of health providers of the subset capable of treating the health need, and
   a ratio of the number of health providers capable of treating the health need to the target number of health providers;
wherein the score is based on a sum of each of the ratios and a total number of health providers in the subset.

14. The non-transitory computer readable storage medium of claim 12, wherein the plurality of health providers includes at least one locked health provider, the at least one locked health provider being initially selected from a set of health providers known to provide high quality health care services, and wherein each subset of health providers includes each of the locked health providers.

15. A method comprising:

receiving patient information describing a plurality of patients;

receiving health guidelines including requirements for filling certain health needs of patients or including a medical practice standard and describing one or more constraints to be satisfied for forming a provider group to treat health needs of the plurality of patients, the one or more constraints including a hard constraint that must be satisfied and a soft constraint that may be satisfied;

identifying a patient population based on the patient information and the health guidelines, the identified patient population having a plurality of health needs;

receiving health provider information describing a plurality of health providers;

selecting a plurality of subsets of health providers from the plurality of health providers according to at least one of the hard constraint or the soft constraint, each health provider of each subset capable of treating at least one health need, the hard constraint requiring a particular type of health provider be included in all subsets of the plurality of subsets, and the soft constraint requiring a particular number of health provider be included based on a size of a user population;

inputting capabilities of each of the plurality of health providers into a first machine learning model;

receiving, as output from the first machine learning model, a respective weight for each respective health provider of the plurality of health providers;

generating, for each subset of health providers of the plurality of subsets, a score using a second machine learning model trained based at least in part on the patient information, the health guidelines, and the health provider information, the score indicating a measurement of a capability of the subset of health providers for treating the plurality of health needs of the identified patient population, the score being determined at least in part based on the respective weights for each respective health provider in each respective subset of health providers; and determining a candidate subset of the plurality of subsets of health providers based at least in part on the scores.

16. The method of claim 15, wherein generating, for each subset of the plurality of subsets, a score comprises:

determining, for each of the plurality of health needs of the identified patient population:
   a target number of health providers to treat the health need,
   a number of health providers of the subset capable of treating the health need, and
   a ratio of the number of health providers capable of treating the health need to the target number of health providers;
wherein the score is based on a sum of each of the ratios and a total number of health providers in the subset.

17. The method of claim 15, wherein the plurality of health providers includes at least one locked health provider, the at least one locked health provider being initially selected from a set of health providers known to provide high quality health care services, and wherein each subset of health providers includes each of the locked health providers.

\* \* \* \* \*

UNITED STATES PATENT AND TRADEMARK OFFICE
CERTIFICATE OF CORRECTION

PATENT NO. : 10,706,964 B2
APPLICATION NO. : 15/339803
DATED : July 7, 2020
INVENTOR(S) : Daniella Jean Perlroth et al.

Page 1 of 1

It is certified that error appears in the above-identified patent and that said Letters Patent is hereby corrected as shown below:

In the Claims

Column 18, Claim 8, Line 15 change "exchange a selected numbers of health providers" to read as --exchange a selected number of health providers--

Signed and Sealed this
Twenty-second Day of December, 2020

Andrei Iancu
*Director of the United States Patent and Trademark Office*